United States Patent
Moon et al.

(10) Patent No.: US 7,038,050 B2
(45) Date of Patent: May 2, 2006

(54) METHOD FOR THE PREPARATION OF HIGHLY PURE 1-ANDROSTENE DERIVATIVES

(75) Inventors: Young Ho Moon, Suwon-si (KR); Dong Jun Kim, Incheon (KR); Chul-Hyun Park, Seongnam-si (KR); Kyung Ik Lee, Anyang-si (KR); Jae-Cheol Lee, Suwon-si (KR); Gwan Sun Lee, Seoul (KR); Young-Kil Chang, Seoul (KR)

(73) Assignee: Hanmi Pharm. Co., Ltd., Kyungki-do (KR)

( * ) Notice: Subject to any disclaimer, the term of this patent is extended or adjusted under 35 U.S.C. 154(b) by 0 days.

(21) Appl. No.: 10/526,158

(22) PCT Filed: Jul. 19, 2004

(86) PCT No.: PCT/KR2004/001786

§ 371 (c)(1),
(2), (4) Date: Mar. 1, 2005

(87) PCT Pub. No.: WO2005/007670

PCT Pub. Date: Jan. 27, 2005

(65) Prior Publication Data

US 2005/0245744 A1    Nov. 3, 2005

(30) Foreign Application Priority Data

Jul. 19, 2003  (KR) .................... 10-2003-0049529

(51) Int. Cl.
*C07D 221/18*  (2006.01)
*C07D 221/02*  (2006.01)

(52) U.S. Cl. ........................................ 546/77; 546/61
(58) Field of Classification Search .................. 546/77, 546/61
See application file for complete search history.

(56) References Cited

U.S. PATENT DOCUMENTS

| 4,760,071 | A | | 7/1988 | Rasmusson et al. |
| 5,084,574 | A | | 1/1992 | Bhattacharya et al. |
| 5,091,534 | A | | 2/1992 | King et al. |
| 5,116,983 | A | | 5/1992 | Bhattacharya et al. |
| 5,120,847 | A | * | 6/1992 | King et al. .................... 546/77 |

FOREIGN PATENT DOCUMENTS

| EP | 0 298 652 A2 | 1/1989 |
| EP | 0 428 366 A2 | 5/1991 |
| EP | 0428366 A | 5/1991 |
| EP | 0 473 225 A2 | 3/1992 |
| EP | 0473225 B1 | 7/1997 |
| KR | 9001206 B1 | 2/1990 |
| KR | 9615038 B1 | 10/1996 |

OTHER PUBLICATIONS

Gary H. Rasmusson et al., "Azasteroids as Inhibitors of Rat Prostatic 5α-Reductase", *J. Med. Chem.*, vol. 27, 1984, pp. 1690-1701.

* cited by examiner

*Primary Examiner*—Charanjit S. Aulakh
(74) *Attorney, Agent, or Firm*—Sughrue Mion, PLLC

(57) ABSTRACT

A method for preparing a 1-androstene derivative which comprises reacting a 2-iodo-androstane derivative with an oxidizing agent while maintaining the pH of the reaction mixture at a specific range gives the 1-androstene derivative with high purity and yield.

6 Claims, No Drawings

METHOD FOR THE PREPARATION OF HIGHLY PURE 1-ANDROSTENE DERIVATIVES

FIELD OF THE INVENTION

The present invention relates to a method for preparing highly pure 1-androstene derivatives.

BACKGROUND OF THE INVENTION

As is well known, 1-androstene derivative is a compound having a double bond between the first and the second carbons of an androstane, and representative drugs having such chemical structure include finasteride and dutasteride.

Finasteride (17β-(N-tert-butylcarbamoyl)-5α-4-aza-androst-1-en-3-one), the compound of formula (II) having an androstene backbone, is known to be effective in treating benign prostatic hyperplasia and androgenic alopecia:

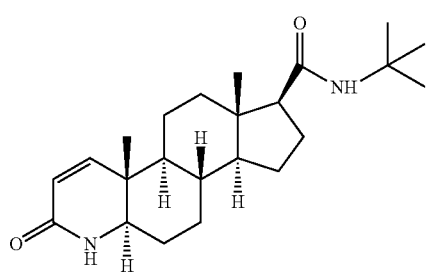

formula (II)

Benign prostatic hyperplasia and androgenic alopecia are caused by binding of excessive 5α-dihydrotestosterone (DHT) derived from testosterone to an androgen receptor. The conversion of testosterone into DHT is accomplished by testosterone 5α-reductase, which can be inhibited by finasteride. Such inhibition of testosterone 5α-reductase by finasteride results in a decreased DHT concentration in plasma and cells, and thus rapid recovery of prostate and increased hair growth. In addition to its effectiveness to benign prostatic hyperplasia and androgenic alopecia, finasteride has excellent drug tolerance and exhibits light, temporary side effects. Currently, finasteride is the only orally administrable product among the two hair-growth agents approved by the United States Food and Drug Administration.

A process for preparing finasteride is disclosed in U.S. Pat. No. 4,760,071 and Korean Patent Publication No. 1990-0001206. As show in Scheme 1, the carboxylic group at the 17β-position of 3-oxo-4-aza-5α-androstane-17β-carboxylic acid of formula (III) is converted into a pyridylthioester group of formula (IV) using 2,2'-pyridyldisulfide. Next, the compound of formula (IV) is reacted with tert-butylamine to obtain 17β-tert-butylcarbamoyl compound of formula (V), followed by introducing a double bond between the first and the second carbon atoms using bezeneselenic anhydride to obtain finasteride of formula (II).

Scheme 1

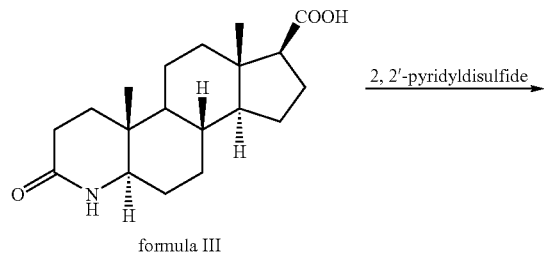

formula III

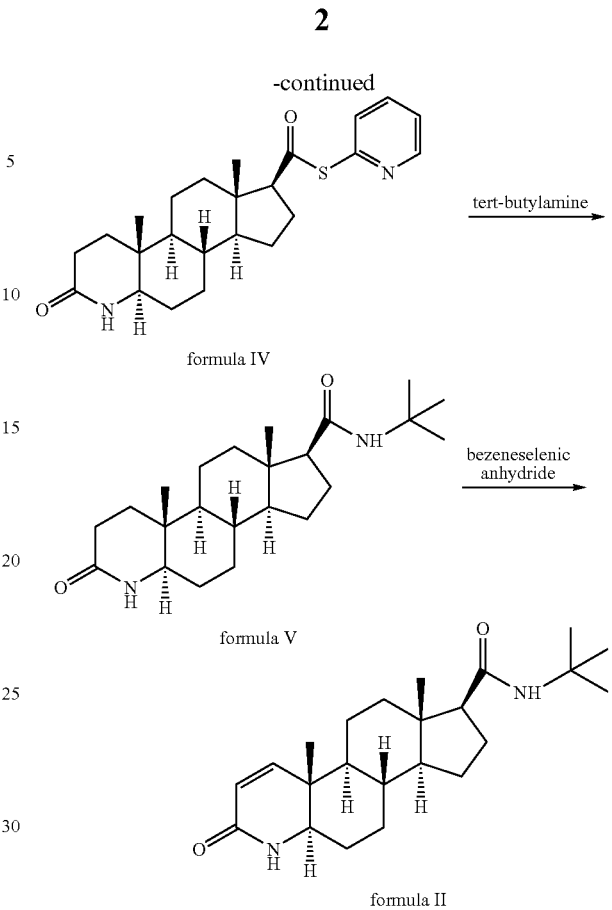

The above process is advantageous in that the dehydrogenation reaction can be accomplished in one step. However, it suffers from a high production cost due to the usage of expensive reagents such as 2,2'-pyridyldisulfide and bezeneselenic anhydride, and a poor purity, e.g., in the range of 75 to 80%, due to the production of undesired by-products. Further, it is difficult to improve the purity of the obtained finasteride even if it undergoes such purification steps as column chromatography and recrystallization.

European Patent No. 298,652, U.S. Pat. Nos. 5,084,574 and 5,116,983, and Korean Patent Publication No. 1996-0015038 disclose a process for preparing finasteride, which comprises silylating the 3-oxo group in the above compound of formula (III) using bistrimethylsilyltrifluoroacetamide (BSTFA), followed by introducing a double bond between the first and the second carbon atoms using 2,3-dichloro-5,6-dicyano-1,4-benzoquinone (DDQ) as an oxidizing agent.

However, this process, in addition to the usage of expensive reagents, has extra problems in that the reaction should be carried out under a nitrogen gas flow and with an anhydrous solvent due to BSTFA's sensitivity to water, and excessive impurities may be produced due to the use of a quinone as an oxidizing agent under reflux condition for 20 hours in a solvent having a high boiling point, i.e., 1,4-dioxane. Further, substantial losses of the obtained product may occur during a purification step, and, therefore, it is not suitable for mass production.

U.S. Pat. No. 5,091,534 and European Patent Nos. 428,366 and 473,225 teach a process for preparing finasteride, which comprises silylating the compound of the above formula (III) in the presence of a base and introducing a halogen such as iodine and bromine into the 2-position of the compound, followed by introducing a double bond between the first and the second carbon atoms using a strong base such as potassium tert-butoxide, 1,8-diazabicyclo[5.4.0]undec-7-ene (DBU) and 1,5-diazabicyclo[4.3.0]non-5-ene (DBN).

However, this process also suffers from a poor purity (about 80%) since the reactants and products tend to be decomposed due to the high pH of the reaction solution containing the strong base, and a low yield after several purification steps (about 30%).

A method for dehydrogenating a 3-oxo-4-azasteroid compound through a sulfinate intermediate is disclosed in *J. Med. Chem.* 27(12): 1690 (1984). First, as shown in Scheme 2, the compound of formula (VI) is reacted with dimethylsulfate to obtain the compound of formula (VII) having a protected amide. Next, the compound of formula (VII) is reacted with diphenyldisulfide in the presence of a strong base such as lithium diisopropylamide (LDA) at −78° C. to produce the compound of formula (VIII) having a phenylsulfide group at the 2-position, and then the amide of the compound of formula (VIII) is deprotected in the presence of a strong acid to obtain the compound of formula (IX). Finally, the compound of formula (X) is prepared by using an oxidizing agent and the compound of formula (XI) is obtained by refluxing the compound of formula (X) in toluene.

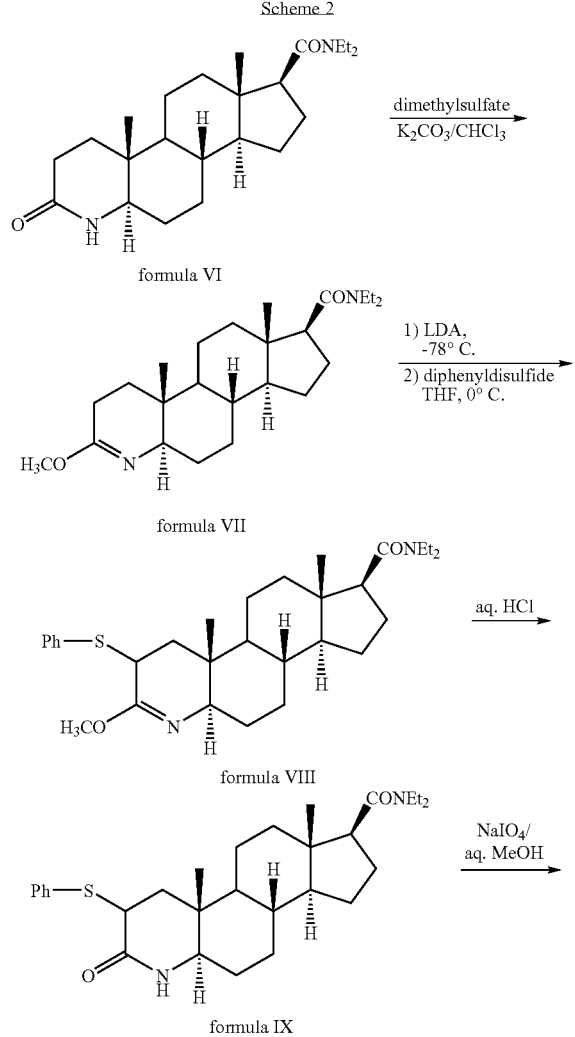

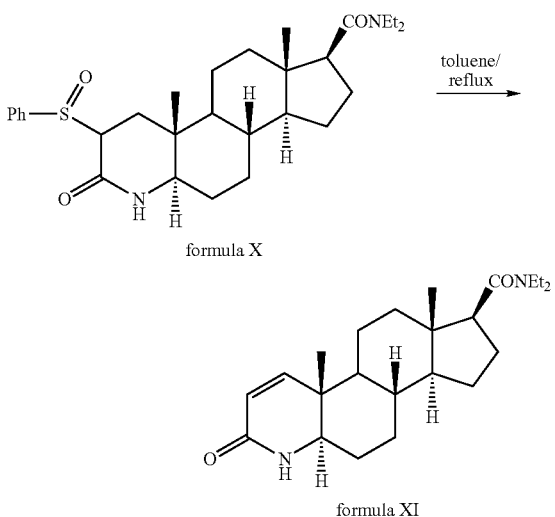

However, this method employs the unnecessary steps of protecting and deprotecfing the amide group, consists of five complicated steps, and uses an inflammable diisopropylamide. Further, it is performed at extremely low temperature, i.e., −78° C., which is not practically applicable to an industrial scale.

As discussed above, the conventional methods for preparing finasteride are disadvantageous in that they employ water-sensitive, expensive or toxic reagents, require extreme reaction conditions or comprise complicated multiple steps, thereby rendering them unsuitable for mass production. Especially, in most conventional methods, finasteride is prepared under a vigorous condition or in the presence of a strong base in a final step, resulting in excessive impurities.

There are strict provisions as to the impurities of finasteride. For example, according to the provision of European Pharmacopeia, the amount of individual impurity A, B and C identified below, may not exceed 0.3% and the total amount of the impurities should not exceed 0.6%. Similarly, according to U.S. Pharmacopeia, the amount of individual impurity A, B and C should not exceed 0.5% and the total amount thereof should not exceed 1.0%.

Impurity A has a structure that the double bond of finasteride is saturated, impurity B has a methylester group at the 17β position, instead of the tert-butylamino group of finasteride, and impurity C contains an extra double bond between the fifth and the sixth carbon atoms.

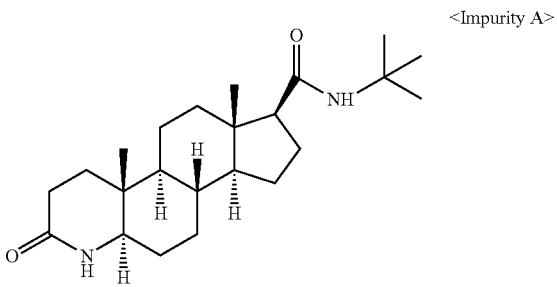

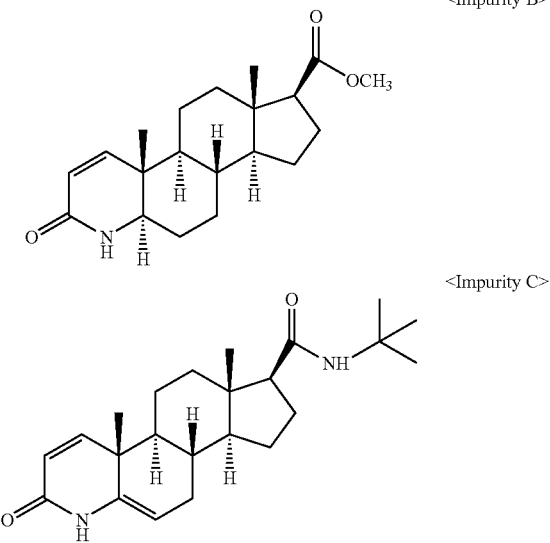

Further, finasteride cannot be easily purified using a conventional method such as recrystallization when it is mixed with an excessive amount of the above impurities A to C, since finasteride and impurities A to C have similar structures. In particular, during the recrystallization of finasteride to meet the amount of impurity A below 0.3%, loss of yield is inevitably caused, thus it renders the final yield of finasteride only 30 to 40%. Further, impurities A and C cannot be easily removed even using column chromatography. Accordingly, there has been a need to develop a method for preparing highly pure 1-androstene derivatives including finasteride.

SUMMARY OF THE INVENTION

It is a primary object of the present invention to provide a method for preparing highly pure 1-androstene derivatives under the mild conditions without using a strong base in a final step.

DETAILED DESCRIPTION OF THE INVENTION

In accordance with one aspect of the present invention, a method for preparing a 1-androstene derivative of formula (I)

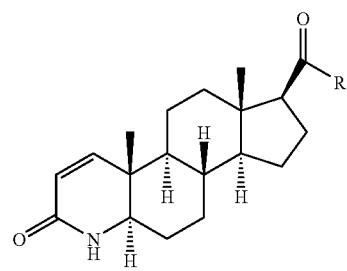

comprises reacting a 2-iodo-androstane derivative of formula (XII)

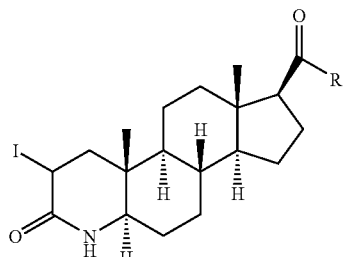

with an oxidizing agent, wherein R is —OH, —OR$^1$ or —NHR$^2$, in which R$^1$ is a straight or branched $C_{1-5}$ alkyl group and R$^2$ is a straight or branched $C_{1-5}$ alkyl group or 2,5-bis(trifluoromethyl)phenyl group.

In the present invention, 1-androstene derivative of formula (I) is prepared by reacting 2-iodo-androstane derivative of formula (XII) with an oxidizing agent to oxidize an iodo group thereof into an iodoxy group, which is easily removed during the reaction, as shown in Scheme 3.

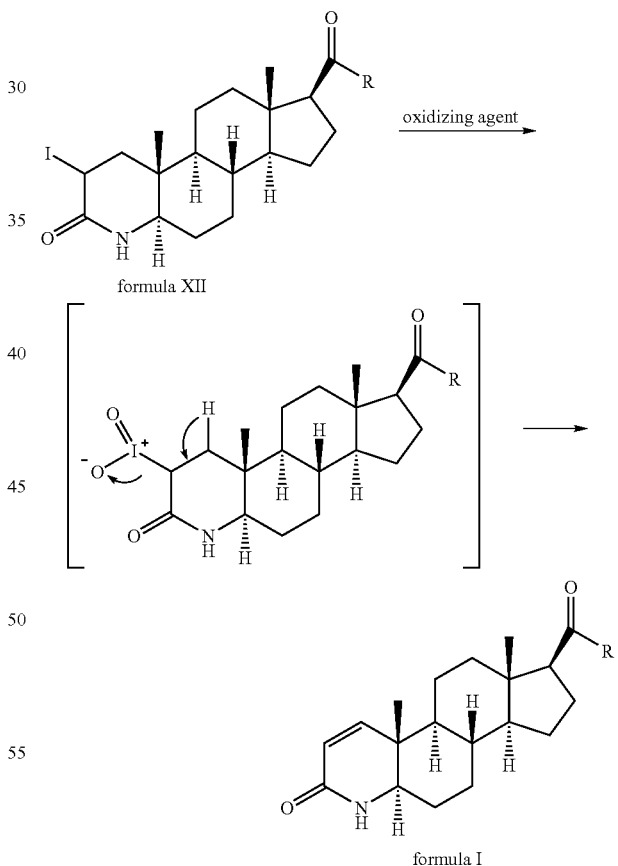

In accordance with the simple method of the present invention, 1-androstene derivatives can be produced in a high purity and yield under mild conditions.

The derivative of formula (XII) used as a starting material of the present invention can be prepared by a conventional method disclosed in European Patent No. 473,225, which comprises reacting an androstane compound, e.g., formula (XIII) with a silylating agent in the presence of a base, followed by reacting with iodine to obtain the derivative of formula (XII),

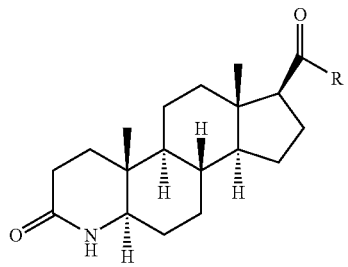

wherein

R is —OH, —OR$^1$ or —NHR$^2$, in which R$^1$ is a straight or branched $C_{1-5}$ alkyl group and R$^2$ is a straight or branched $C_{1-5}$ alkyl group or 2,5-bis(trifluoromethyl)phenyl group.

In the present invention, the compound of formula (XIIIa) corresponding to the compound of formula (XIII) wherein R is tert-butylamino may be prepared by a method shown in Scheme 4 (see Korean Patent Application No. 2003-20671).

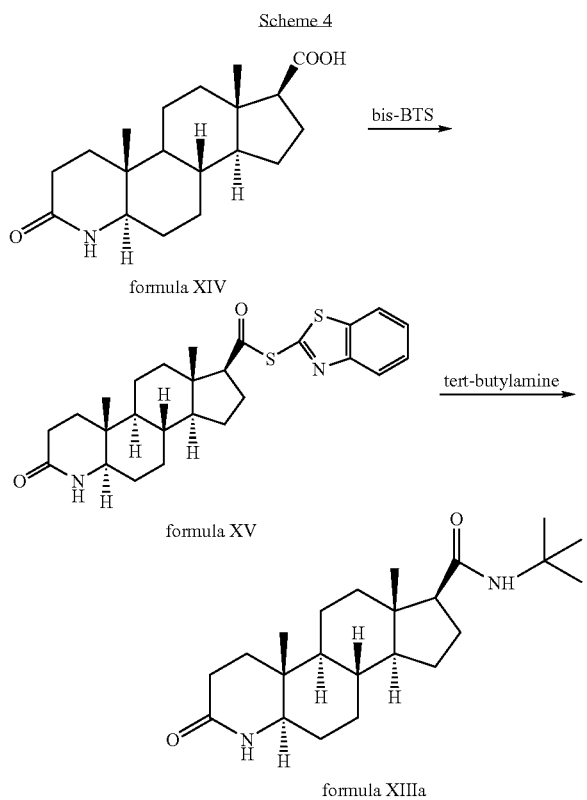

The oxidizing agent which may be used in the present invention includes m-chloroperbenzoic acid, peracetic acid, trifluoroperacetic acid, permaleic acid, sodium bromite, sodium hypochloride, hydrogen peroxide, iodosomethylbenzene and iodosobenzene; and m-chloroperbenzoic acid is most preferred.

In a preferred embodiment of the present invention, the oxidizing agent may be employed in an amount ranging from 2.0 to 6.0 equivalents, preferably 3.0 to 4.0 equivalents based on 1.0 equivalent of the derivative of formula (XII).

In the present invention, the total amount of the oxidizing agent may be added at a time during an early step of the reaction, or in divided amounts, e.g., ranging from ¼ to ½ of the total amount, at intervals of 30 to 60 minutes.

The organic solvent which may be used in the present invention includes at least one solvent selected from the group consisting of tetrahydrofuran, dioxane, acetonitrile, dimethylacetamide, dimethylformamide and dimethylsulfoxide; and tetrahydrofuiran is most preferred.

The method of the present invention can be accomplished by using the oxidizing agent alone. However, if free acids produced during the reaction, i.e., m-chlorobenzoic acid and iodic acid when m-chloroperbenzoic acid is used as an oxidizing agent, remain in the reactant mixture without any neutralizing step, the pH of the reaction solution may decrease, and thus the reactants, products and reagents may decompose, thereby producing undesired by-products. On the other hand, if the reaction is conducted at a pH in the range of 5.5 to 7.5, the reaction can be completed with substantially less by-products.

The reaction of the present invention may be carried out at a temperature in the range of 0 to 50° C., preferably 15 to 30° C.

Although the time period for completing the present reaction may vary with the reaction temperature or the amount of the oxidizing agent used, about 8 to 24 hours may be sufficient.

Thus, in accordance with the simple method of the present invention, 1-androstene derivatives can be produced with high purity and yield over 80% under mild conditions. Further, the method of the present invention employs short reaction steps, and, therefore, is suitable for mass production.

The present invention will be described in further detail with reference to Examples. However, it should be understood that the present invention is not restricted by the specific Examples.

PREPARATION EXAMPLE 1

Preparation of benzothiazolyl 3-oxo-4-aza-5α-androstane-17β-thiocarboxylate 200 g of 3-oxo-4-aza-5α-androstane-17β-carboxylic acid and 250 g of bisbenzothiazolylthioester (bis-BTS) were mixed in 3 l of methylenechloride, and stirred at room temperature for 30 minutes. 197 g of triphenylphosphine was added thereto, stirred for 30 minutes and 105 ml of triethylamine diluted with 200 ml of methylenechloride was added dropwise thereto over a period of 30 minutes, followed by stirring the mixture at room temperature for 4 hours. The precipitation formed was filtered, washed successively with methylenechloride and diethylether, and dried at 40° C. overnight to obtain 281 g of the title compound (yield: 96%) as a pale white solid.

m.p.: 245~247° C.; $^1$H-NMR (300 MHz, CDCl$_3$, δ); 8.02 (d, 1H), 7.91 (d, 1H), 7.50 (m, 2H), 5.54 (brs, 1H), 3.06 (dd, 1H), 2.76 (t, 1H), 2.45 (m, 2H), 2.26 (m, 2H), 1.9 (m, 2H), 1.75 (m, 2H), 1.65 (m, 1H), 1.51~1.34 (m, 7H), 1.21 (m, 1H), 1.12 (m, 1H), 0.91 (s, 3H), 0.81 (m, 1H), 0.79 (s, 3H)

PREPARATION EXAMPLE 2

Preparation of N-(tert-butyl)-3-oxo-4-aza-5α-androstane-17β-carboxamide (compound of formula (XIIIa))

281 g of benzothiazolyl 3-oxo-4-aza-5α-androstane-17β-thiocarboxylate obtained in Preparation Example 1 was added to 2.8 l of dimethylformamide and 315 ml of tert-butylamine was added thereto, followed by stirring the mixture at 50° C. for 4 hours. The resultant was cooled to about 10° C., 5.6 l of water was slowly added thereto and stirred at room temperature for an hour. The precipitation formed was filtered, washed successively with water and isopropylether, and dried at 40° C. overnight to obtain 206 g of the title compound (yield: 92%) as a pale white solid.

m.p.: 280~284° C.; $^1$H-NMR (300 MHz, CDCl$_3$, δ); 5.66 (brs, 1H), 5.07 (brs, 1H), 3.07 (dd, 1H), 2.41, (m, 2H), 2.12 (m, 2H), 2.10~1.80 (m, 3H), 1.8~1.52 (m, 4H), 1.51~1.41 (m, 4H), 1.35 (s, 9H), 1.3~1.18 (m, 2H), 1.15~0.92 (m, 2H), 0.91 (s, 3H), 0.90~0.70 (m, 1H), 0.69 (s, 3H)

PREPARATION EXAMPLE 3

Preparation of N-(tert-butyl)-2-iodo-3-oxo-4-aza-5α-androstane-17β-carboxamide (compound of formula (XII) wherein R is tert-butylamino)

205 g of N-(tert-butyl)-3-oxo-4-aza-5α-androstane-17β-carboxamide obtained in Preparation Example 2 and 248 ml of tetramethylethylenediamine were added to 2 l of toluene, cooled to 0° C., 138 ml of trimethylchlorosilane was added dropwise thereto, and stirred for 30 minutes. 208 g of iodine was added thereto in 1/4 portions every 30 minute over a period of 2 hours, followed by stirring the mixture for 2 hours. 2 l of 10% sodium thiosulfate was added dropwise to the mixture and stirred overnight. The precipitation formed was filtered, washed successively with water and isopropylether, and dried at 40° C. overnight to obtain 255 g of the title compound (yield: 93%) as an white solid.

m.p.: 218~220° C.; $^1$H-NMR (300 MHz, CDCl$_3$, δ); 5.82 (brs, 1H), 5.06 (brs, 1H), 4.75 (dd, 1H), 3.15 (dd, 1H), 2.56 (dd, 1H), 2.20~1.88 (m, 4H), 1.80~1.36 (m, 8H), 1.34 (s, 9H), 1.32~1.12 (m, 2H), 1.10~0.90 (m, 2H), 0.88 (s, 3H), 0.85 (m, 1H), 0.67 (s, 3H)

EXAMPLE 1

Preparation of N-(tert-butyl)-3-oxo-4-aza-5α-androstene-17β-carboxamide (finasteride: compound of formula (II))

244 g of N-(tert-butyl)-2-iodo-3-oxo-4-aza-5α-androstane-17β-carboxamide obtained in Preparation Example 3 was added to a mixture of 2.4 l of tetrahydrofuran and 1.4 l of saturated sodium bicarbonate. 112 g of m-chloroperbenzoic acid (content: maximum 75%) was added thereto in ¼ portions every 1 hour, followed by stirring the mixture overnight. After completion of the reaction, pH of the mixture was adjusted to about 7 using saturated sodium bicarbonate, followed by stirring the mixture for an hour. The precipitation formed was filtered and the crude product was dissolved in 1.5 l of methylenechloride, washed successively with 1.5 l of 10% sodium sulfite (2 times) and 1.5 l of water. The isolated methylenechloride layer was dried, filtered and the solvent was evaporated off. The resulting residue was refluxed in 435 ml of isopropylacetate for an hour, cooled to room temperature, filtered and washed with ether. The precipitate formed was dispersed in a mixture of 2.25 l of water and 250 ml of acetic acid, stirred at 50° C. for 2 hours, cooled to room temperature, filtered and washed with water. Then, the precipitation was dried at 40° C. overnight to obtain 148.6 g of the title compound (yield: 82%) as an white solid.

m.p.: 257~259° C.; purity: 99.8% (HPLC); impurity A: 0.07%, impurity B: 0%, impurity C: 0.05%;

$^1$H-NMR (300 MHz, $^1$H-NMR CDCl$_3$) δ6.82(d, 1H), 5.81(d, 1H), 5.49(brs, 1H), 5.10(brs, 1H), 3.34(dd, 1H), 2.21(t, 1H), 2.01(m, 2H), 1.80~1.60(m, 7H), 1.34(s, 9H), 1.50–1.26(m, 5H), 1.07–1.00(m, 3H), 0.98(s, 3H), 0.71(s, 3H)

EXAMPLE 2

Preparation of N-(tert-butyl)-3-oxo-4-aza-5α-androstene-17β-carboxamide (finasteride: compound of formula (II))

244 g of N-(tert-butyl)-2-iodo-3-oxo-4-aza-5α-androstane-17β-carboxamide obtained in Preparation Example 3 was added to a mixture of 2.0 l of tetrahydrofuran and 2.0 l of saturated sodium bicarbonate. 141 g of m-chloroperbenzoic acid (content: maximum 75%) was added thereto in 1/3 portions every 1 hour, followed by stirring the mixture overnight. Thereafter, 145.2 g of the title compound (yield: 80%) was obtained as a white solid in accordance with Example 1.

Purity: 99.7% (HPLC); impurity A: 0.09%, impurity B: 0%, impurity C: 0.07%;

$^1$H-NMR data was the same as Example 1

COMPARATIVE EXAMPLE 1

Preparation of N-(tert-butyl)-3-oxo-4-aza-5α-androstene-17β-carboxamide (finasteride: compound of formula (II)) without maintaining pH of the reactant solution in the range of 5.5 to 7.5

244 g of N-(tert-butyl)-2-iodo-3-oxo-4-aza-5α-androstane-17β-carboxamide obtained in Preparation Example 3 was dissolved in 2.4 l of tetrahydrofuran. 141 g of m-chloroperbenzoic acid (maximum content: 75%) was added thereto in ⅓ portions every 1 hour, followed by monitoring the process of the reaction using thin layer chromatography (TLC). The color of the reactant solution gradually became dark black, pH thereof was drop to below 4, and a large amount of undesired impurities were produced. The reaction was terminated at hour 6 when the reaction was not yet completed. Thereafter, 136.1 g of the crude title compound (yield: 75%) was obtained as a yellow solid in accordance with Example 1.

Purity: 52.7% (HPLC); impurities: unreacted compound obtained in Preparation Example 3=4.6%, unidentified compound=39.2%, impurity A=2.8%, impurity B=0%, impurity C=0.65%

COMPARATIVE EXAMPLE 2

Preparation of N-(tert-butyl)-3-oxo-4-aza-5α-androstene-17β-carboxamide (finasteride: compound of formula (II)) in accordance with the prior method disclosed in European Patent Nos. 428,366 and 473,225

8.0 g of potassium t-butoxide was dispersed in 20 ml of N,N-dimethylformamide (DMF), cooled to −10° C. and 3.5 g of N-(t-butyl)-2-iodo-3-oxo-4-aza-5α-androstene-17β-carboxamide dissolved in 15 ml of DMF was added dropwise thereto while maintaining the same temperature. The mixture was stirred vigorously for 10 minutes and the reaction was quenched by the dropwise addition of 7.2 ml of acetic acid while maintaining the reaction temperature of below 10° C. After stirring the mixture for 5 minutes, 200 ml of 20% sodium chloride was slowly added thereto at 0° C. The resulting solution was stirred overnight at 0° C., filtered, washed and dried under a vacuum at 60° C. The crude product (HPLC purity: 75%) was refluxed in 20 ml of isopropylacetate for an hour, cooled, filtered and washed with ether. The precipitate formed was dispersed in the mixture of 45 ml of water and 5 ml of acetic acid, stirred at 50° C. for 2 hours, cooled to room temperature, filtered and washed with water. Then, the precipitate was dried at 40° C. overnight to obtain 0.96 g of the title compound (yield: 37%) as an white solid.

m.p.: 256~159° C.; purity: 98.1% (HPLC); impurity A=0.9%, impurity B=0%, impurity C=0.45%; $^1$H-NMR data was the same as Example 1

While the invention has been described with respect to the above specific embodiments, it should be recognized that various modifications and changes may be made to the invention by those skilled in the art which also fall within the scope of the invention as defined by the appended claims.

What is claimed is:

1. A method for preparing a 1-androstene derivative of formula (I)

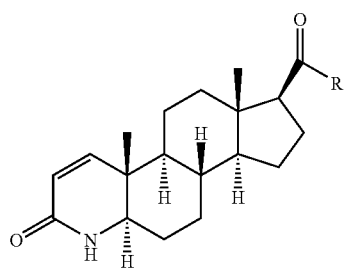

(I)

which comprises reacting a 2-iodo-androstane derivative of formula (XII)

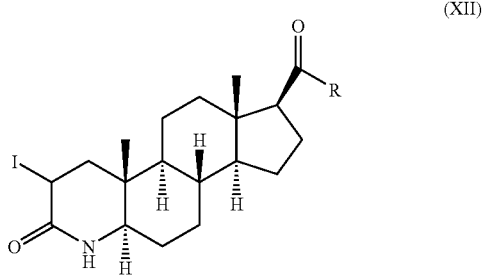

(XII)

with an oxidizing agent, wherein R is —OH, —OR$^1$ or —NHR$^2$, in which R$^1$ is a straight or branched C$_{1-5}$ alkyl group and R$^2$ is a straight or branched C$_{1-5}$ alkyl group or 2,5-bis(trifluoromethyl)phenyl group.

2. The method of claim 1, wherein the oxidizing agent is selected from the group consisting of m-chloroperbenzoic acid, peracetic acid, trifluoroperacetic acid, permaleic acid, sodium bromite, sodium hypochloride, hydrogen peroxide, iodosomethylbenzene and iodosobenzene.

3. The method of claim 1 or 2, wherein the oxidizing agent is m-chloroperbenzoic acid.

4. The method of claim 1, wherein the oxidizing agent is employed in an amount ranging from 2.0 to 6.0 equivalents based on 1.0 equivalent of the derivative of formula (XII).

5. The method of claim 1, wherein the reaction is conducted at a pH ranging from 5.5 to 7.5.

6. The method of claim 1, wherein R is tert-butylamino or 2,5-bis(trifluoromethyl)phenylamino.

* * * * *